United States Patent
Neggiani et al.

(10) Patent No.: US 11,123,354 B2
(45) Date of Patent: Sep. 21, 2021

(54) METHOD FOR THE TREATMENT OF OSTEOARTHRITIS

(71) Applicant: ABIOGEN PHARMA S.P.A., Loc. Ospedaletto Pisa (IT)

(72) Inventors: Fabio Neggiani, Pisa (IT); Silvia Trasciatti, Madonna Dell'Acqua-San Giuliano Terme (IT)

(73) Assignee: ABIOGEN PHARMA S.P.A., Loc. Ospedaletto (IT)

( * ) Notice: Subject to any disclaimer, the term of this patent is extended or adjusted under 35 U.S.C. 154(b) by 0 days.

(21) Appl. No.: 16/467,207

(22) PCT Filed: Dec. 6, 2017

(86) PCT No.: PCT/IB2017/057685
§ 371 (c)(1),
(2) Date: Jun. 6, 2019

(87) PCT Pub. No.: WO2018/104879
PCT Pub. Date: Jun. 14, 2018

(65) Prior Publication Data
US 2020/0061088 A1    Feb. 27, 2020

(30) Foreign Application Priority Data
Dec. 6, 2016   (IT) .................. 102016000123773

(51) Int. Cl.
| | |
|---|---|
| *A61K 31/663* | (2006.01) |
| *A61P 19/02* | (2006.01) |
| *A61K 9/00* | (2006.01) |
| *A61K 9/08* | (2006.01) |
| *A61K 47/02* | (2006.01) |

(52) U.S. Cl.
CPC .......... *A61K 31/663* (2013.01); *A61K 9/0019* (2013.01); *A61K 9/08* (2013.01); *A61K 47/02* (2013.01); *A61P 19/02* (2018.01)

(58) Field of Classification Search
CPC .............................. A61K 31/663; A61P 19/02
See application file for complete search history.

(56) References Cited

U.S. PATENT DOCUMENTS 4,814,326 A * 3/1989 Rosini .................... A61K 31/66
514/108

FOREIGN PATENT DOCUMENTS

| EP | 1136069 A1 | 9/2001 |
|---|---|---|
| EP | 2668952 A2 | 12/2013 |
| WO | 2007073921 A1 | 7/2007 |

OTHER PUBLICATIONS

Cocco R., et al., "Effects of clodronate on synovial fluid levels of some inflammatory mediators, after intra-articular administration to patients with synovitis secondary to knee osteoarthritis", Bollettino della Societa' Italiana di Biologia Sperimentale—Bullettin of the Italian Society of Experimental Bio, vol. 75, No. 11/12, Nov. 1, 1999, pp. 71-76.
Search Report and Written Opinion of PCT/IB2017/057685 dated Mar. 12, 2018.
European Office Action dated Mar. 23, 2021 for corresponding european application No. 17825933.9.
Indian Office Action dated Jan. 12, 2021 in connection with corresponding Indian Application No. 201917026745.
Rossin M.I et al., "Intra-articular clodronate for the treatment of knee osteoarthritis: dose range study vs. hyaluronic acid", Rheumatology 2009; 48:-773-778.
Rossini M. et al., "Effects of intra-articular clodronate in the treatment of kee osteoarthritis: results of a double-blind, randomized placebo-controlled trial", Rheumatol. Int (2015) 35:255-263.

* cited by examiner

*Primary Examiner* — Kevin E Weddington
(74) *Attorney, Agent, or Firm* — Silvia Salvadori, P.C.; Silvia Salvadori

(57) ABSTRACT

The present invention relates to a composition for use in the treatment of osteoarthritis (OA), wherein said composition comprises from 5 to 40 mg of sodium chlodronate, or an equivalent amount of chlodronic acid, or other pharmaceutically acceptable salts thereof, and wherein said composition is administered intra-articularly in a unitary dosage form once monthly, once biweekly or once weekly. Single-dose medicaments and kits comprising them are also described.

23 Claims, 3 Drawing Sheets

METHOD FOR THE TREATMENT OF OSTEOARTHRITIS

This application is a U.S. national stage of PCT/IB2017/057685 filed on 6 Dec. 2017, which claims priority to and the benefit of Italian Patent Application No. 102016000123773, filed on 6 Dec. 2016, the contents of which are incorporated herein by reference in their entireties.

FIELD OF THE INVENTION

The invention concerns a pharmaceutical composition for use by intra-articular route for the treatment of osteoarthritis (OA) comprising sodium chlodronate, or an equivalent amount of chlodronic acid, or other pharmaceutically acceptable salts thereof.

TECHNICAL FIELD

Arthritis or osteoarthritis (OA) is a chronic, progressive disease that particularly affects joints that are more prone to mechanical stress, such as hips and knees. When this condition occurs, the whole joint is affected by a series of degradative and reparative processes that ultimately alter the anatomy and function of the joint itself by affecting all the articular components, such as cartilage, subchondral bone, and synovial tissues. The "arthritic" condition is therefore the result of a set of interrelations among systemic factors (e.g., advanced age, obesity) and local factors (e.g., traumas, excessive use) modulated in turn by numerous predisposing factors on which infectious and inflammatory events of various etiologies can add on.

In this complexity of events it has been tried, over time, to intervene therapeutically by addressing and counteracting the individual causal processes and resorting to a variety of different therapeutic approaches, essentially oriented to the management of inflammatory events and the pain caused, mainly using analgesics, local or systemic anti-inflammatories, or intra-articular injections of various drugs such as, for example, bisphosphonates, hyaluronic acid, anthraquinones, chondroitin sulfate. The patent EP0203649, owned by Istituto Gentili, describes, for example, compositions for use in osteoarthritis, to be administered by intra-articular route (i.a.) comprising bisphosphonates, preferably sodium chlodronate. In particular, the document describes aqueous preparations containing bisphosphonates in low concentrations, ranging from $10^{-1}$ to $10^{-6}$ M, with pH comprised between 4.5 and 7.5, made isotonic by means of sodium chloride or other similar excipients. In particular, the document describes the technical problem connected to the stability of these preparations, solved thanks to the addition of amino acids, preferably glycine or lysine.

The described preparations are formulated in an aqueous solvent, ready-to-use, or in the form of a lyophilizate to be reconstituted in the solvent at the time of use. In all the examples reported, relating to formulations comprising sodium chlodronate in a 1 mg or 0.5 mcg dosage, glycine is used as a stabilizing agent for the solution. According to the teachings provided by EP0203649, the possibility of formulating pharmaceutically stable sodium chlodronate solutions is, in fact, conditioned by the addition of stabilizers to prevent the precipitation of chlodronate, which is also marked at the low concentrations used in the described preparations.

The publication by Cocco et al. (J. Biol. Res., Boll. Soc. It. Biol. Sper., 1999, N. 11-12-Vol. LXXV-Idelson-Naples) describes a study conducted on 20 patients with osteoarthritis of the knee, treated with a cycle of IA injections of sodium chlodronate at a dose of 0.9 mg, for a total period of 21 days, specifically administered on days 1, 3, 7, 10, 14, and 21. The study demonstrated a marked positive effect of the described treatment on pain symptoms, in particular with reference to spontaneous pain and pain in movement, and particularly in correspondence to the injection performed on day 3.

The study concludes with the need of carrying out clinical trials to determine the actual benefits of the treatment compared to traditional therapies.

It should be noted, however, that the indicated treatment is to be considered highly invasive in terms of compliance, considering the pain of injections that, according to the dosing schedule, should be administered to the patient for as many as 6 times in just 3 weeks.

In fact, as it is apparent from the above-mentioned documents, even today, the main therapeutic objective in the treatment of OA is the management and reduction of the pain symptoms that always accompany this pathology, and that make the quality of life of the affected patients critical, a goal to be reached hopefully through therapeutic approaches that are as least invasive as possible.

The research is, therefore, constantly aimed at identifying new drugs, or new dosages and/or therapeutic schemes of known drugs, that exhibit a specific efficacy in the treatment of OA, and in particular in the treatment of OA pain symptoms, while guaranteeing a high patient compliance.

Therefore, the object of the present invention is to provide a new therapeutic alternative for the treatment of OA, and in particular for the treatment of OA pain symptoms, which is at the same time efficacious, safe, and with a satisfactory compliance for the patient.

SUMMARY

The inventors of the present invention have surprisingly found that a pharmaceutical composition comprising from 5 to 40 mg of sodium chlodronate, or an equivalent amount of chlodronic acid, or other pharmaceutically acceptable salts thereof, could be used in the treatment of osteoarthritis (OA) by intra-articular administration as a unitary dosage form once monthly, or once biweekly, or once weekly.

In particular, said composition in a unitary dosage form allowed the treatment of osteoarthritis pain symptoms (OA).

With the present invention, the inventors have demonstrated a new type of therapeutic approach for the treatment of OA, and in particular of OA pain symptoms, thanks to the verified possibility and effectiveness of intra-articular administration of unitary dosage forms comprising from 5 to 40 mg of sodium chlodronate, or an equivalent amount of chlodronic acid, or other salts thereof, to be administered monthly, biweekly, or weekly, preferably monthly.

In a preferred embodiment of the pharmaceutical composition for the use of the invention, said composition administered in a unitary dosage form preferably comprises from 5 to 20 mg, more preferably from 8 to 20 mg, of sodium chlodronate or an equivalent amount of chlodronic acid, or other salts thereof, and optionally suitable pharmacologically acceptable excipients.

In a further preferred embodiment, said pharmaceutical composition for use in a unitary dosage form, comprises from 30 to 40 mg of sodium chlodronate, or an equivalent amount of chlodronic acid, or other salts thereof, and suitable excipients. In another aspect, the present invention concerns a single dose medicament consisting of a container selected from the group consisting of a vial, bottle, carpule, or a pre-filled syringe, and a composition contained in said container and comprising from 5 to 40 mg of sodium chlodronate, or an equivalent amount of chlodronic acid, or other salts thereof, and optionally pharmacologically acceptable excipients. The single dose medicament of the invention is advantageously for use in the treatment of osteoarthritis (OA), wherein said medicament is administered intra-articularly in a unitary dosage form once monthly, or once biweekly, or once weekly.

In yet another aspect, the present invention relates to a kit comprising from 1 to 4, preferably from 1 to 2, even more preferably 1 single dose medication consisting of a container selected from the group consisting of a vial, bottle, carpule, or pre-filled syringe, and a composition contained in said container and comprising a unitary dosage form from 5 to 40 mg of sodium chlodronate, or equivalent dosages of the corresponding chlodronic acid, or other salts thereof, and optionally suitable pharmacologically acceptable excipients. The kit of the invention therefore comprises single use medicaments for intra-articular administration once monthly, or once biweekly, or once weekly for the treatment of patients with OA.

The inventors have also shown that said compositions, having a high concentration of sodium chlodronate, result to be particularly stable in aqueous solution, if formulated so as to obtain osmolality values of between 380 and 420 mOsm/Kg, preferably between 385 and 415 mOsm/Kg.

In yet another aspect, therefore, the invention relates to a pharmaceutical composition in the form of an aqueous solution comprising from 5 to 40 mg/ml of sodium chlodronate, or an equivalent amount of the corresponding chlodronic acid or other salts thereof, and suitable excipients, said composition having osmolality values in the range from 380 to 420 mOsm/Kg, preferably from 385 to 415 mOsm/Kg.

BRIEF DESCRIPTION OF THE FIGURES

The characteristics and the advantages of the present invention will be apparent from the following detailed description, from the embodiments provided as illustrative and non-limiting examples, and from the attached figures wherein.

DETAILED DESCRIPTION OF THE INVENTION

Figure 1:
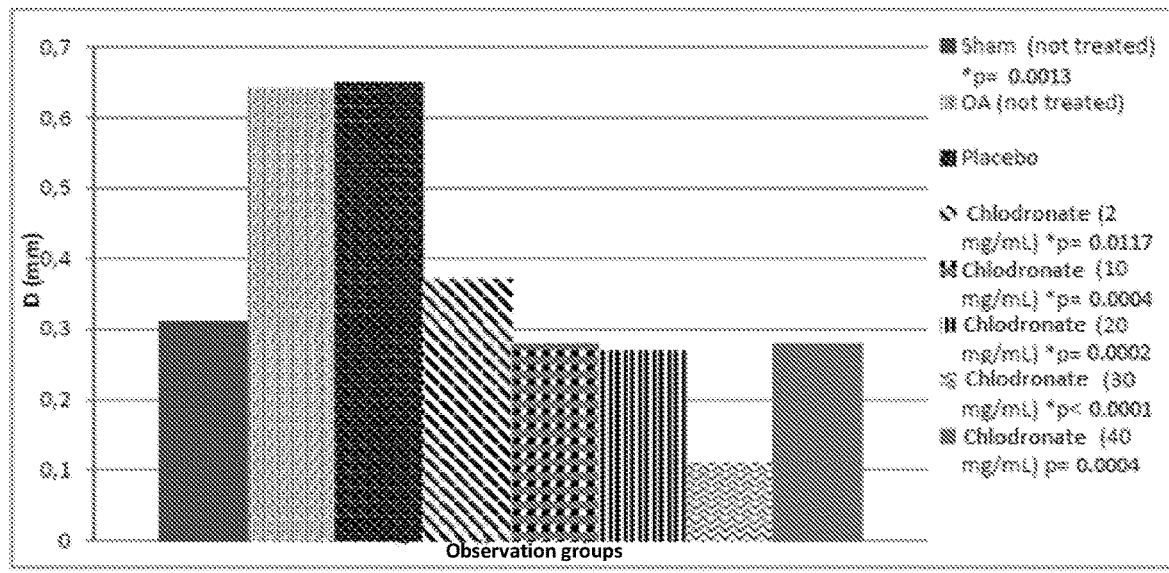
FIG. 1 shows the efficacy results obtained, expressed as the mean value of the difference in the size of the edema present in the two inflamed rat knees, after weekly treatment with sodium chlodronate at the concentrations of 2, 10, 20, 30 and 40 mg/ml, in the 8 observation groups.

The invention therefore concerns a pharmaceutical composition for use in the treatment of osteoarthritis (OA), wherein said composition comprises from 5 to 40 mg of sodium chlodronate, or an equivalent amount of chlodronic acid, or other pharmaceutically acceptable salts thereof, and wherein said composition is administered intra-articularly in a unitary dosage form once monthly, or once biweekly, or once weekly.

For the purposes of the present invention, the term "sodium chlodronate, or chlodronic acid, or other salts thereof" is intended to include all their polymorphic forms, both amorphous and crystalline, and co-crystalline, as well as anhydrous, hydrated, and solvate forms.

Preferably, the composition for use in the treatment of osteoarthritis (OA) of the invention is directed to the treatment of pain symptoms of osteoarthritis (OA). In a preferred embodiment of the pharmaceutical composition for the use of the invention, said composition, administered in a unitary dosage form, preferably comprises from 5 to 20 mg, more preferably from 8 to 20 mg, of sodium chlodronate or an equivalent amount of chlodronic acid, or other salts thereof, and optionally suitable pharmacologically acceptable excipients.

In a further preferred embodiment, said pharmaceutical composition for use in a unitary dosage form, comprises from 30 to 40 mg of sodium chlodronate, or an equivalent amount of chlodronic acid, or other salts thereof.

Preferably, said sodium chlodronate in all embodiments is in tetrahydrate form.

Suitable pharmaceutically acceptable excipients for intra-articular administration are, for example, pH regulators, isotonic regulators, stabilizers, chelating agents, preservative agents, and antioxidants.

Preferred pH regulators are citric acid, sodium citrate, sodium acetate, boric acid, sodium borate, sodium bicarbonate, phosphoric acid and salts thereof, even more preferably citric acid and sodium citrate (citrate buffer), and sodium bicarbonate.

Among isotonic regulators, sodium chloride or dextrose are preferred.

Among stabilizers, mannitol, dextran, or mixtures thereof are preferred.

Among chelating agents, EDTA or a salt thereof, such as EDTA sodium, are preferred.

Among antioxidants, sodium metabisulfite, potassium metabisulfite, sodium bisulfite, butylated hydroxyanisole (BHA), butylated hydroxytoluene (BHT), ascorbic acid, and sodium ascorbate are preferred.

Among preservative agents, benzyl alcohol, methyl paraben, and propyl paraben are preferred.

In a preferred embodiment, said pharmaceutical composition for use comprises sodium chlodronate, sodium bicarbonate, and sodium chloride.

In a further preferred embodiment, said pharmaceutical composition in a unitary dosage form comprises from 5 to 40 mg of sodium chlodronate, or equivalent dosages of the corresponding chlodronic acid, or other salts thereof, sodium bicarbonate, citrate buffer, and sodium chloride.

In a preferred and advantageous embodiment, the composition for the use of the invention is administered intra-articularly in a unitary dosage form once a month.

In a further preferred and advantageous embodiment, the composition for the use of the invention is administered intra-articularly in a unitary dosage form once every two weeks.

In yet another embodiment, the composition for the use of the invention is administered intra-articularly in a unitary dosage form once a week.

Preferably the composition of the invention is in the form of an aqueous solution in an overall volume of 1 to 3 ml, preferably in an overall volume of about 1 ml. Even more preferably, said composition in the form of an aqueous solution has a pH value from 3.5 to 5.5, preferably from 4.0 to 5.0, even more preferably from 4.3 to 4.7.

All the pharmaceutical compositions for the uses described above may be prepared by methods known in the art in relation to the specific route of administration.

In another aspect, the present invention concerns a single dose medicament.

For the purposes of the present invention, single dose medicament means a container selected from the group consisting of a vial, a bottle, a carpule, and a pre-filled syringe, which contains a composition comprising a unitary dosage form from 5 to 40 mg of sodium chlodronate, or an equivalent amount of chlodronic acid, or other salts thereof, and optionally pharmacologically acceptable excipients.

The single dose medicament of the invention is advantageously for use in the treatment of osteoarthritis (OA), wherein said medicament is administered by intra-articular route in a unitary dosage form once monthly, or once biweekly, or once weekly.

The composition of the single dose medicament of the invention, and contained in the container, is preferably in the form of an aqueous solution ready for use. More preferably, said aqueous solution has a volume from 1 to 3 ml, preferably equal to about 1 ml.

Even more preferably, such aqueous solution is a ready-to-use aqueous solution comprising from 30 to 40 mg of sodium chlodronate in a volume of 1 ml.

Advantageously, said medicament is administered monthly.

Since the medicament may comprise the composition for the use of the invention, all the preferred aspects of the composition are preferred also for the single use medicament.

The invention therefore concerns a single dose medicament for use in the treatment of osteoarthritis, wherein said medicament is administered intra-articularly once a month.

In yet another aspect, the present invention relates to a kit comprising from 1 to 4, preferably from 1 to 2, even more preferably 1, single dose medicaments of the invention.

The kit of the invention is advantageously for use in the treatment of osteoarthritis (OA), for which it will contain a number from 1 to 4 single use medicaments for intra-articular administration of the same medicament once monthly, or once biweekly, or once weekly. The kit of the invention may advantageously contain an illustrative leaflet for the use of the medicament, and therefore of the composition of the invention.

It is to be understood that all the aspects identified as preferred and advantageous for the composition are to be considered similarly preferred and advantageous also for the kit comprising said single use medicament, i.e. a vial, bottle, carpule, or pre-filled syringe, and respective uses thereof.

In a further aspect, the invention finally relates to a pharmaceutical composition in the form of an aqueous solution comprising from 5 to 40 mg/ml of sodium chlodronate, or equivalent amounts of chlodronic acid or other salts thereof, and suitable excipients, having an osmolality value in the range from 380 to 420 mOsm/Kg, preferably from 385 to 415 mOsm/Kg.

Osmolality values were determined according to USP, chapter 275 under the heading "Osmolality and Osmolarity".

Among the excipients that may be used to regulate osmolality in the specific range of values indicated, substances commonly known as osmolality regulators may be used, suitable in particular for injectable preparations, such as for example dextrose, mannitol and sodium chloride, preferably sodium chloride.

Examples of embodiments of the present invention are given below by way of exemplary and non-limiting example.

EXAMPLES

Example 1

This study was aimed at demonstrating the efficacy in the treatment of OA of the administration of high doses of sodium chlodronate, specifically up to values of 40 mg/ml per each single administration.

As an experimental model of OA induction, one involving the intra-articular administration of MIA (monosodium iodoacetate) was used.

The IA injection of MIA creates a model of acute inflammation that allows the study of cartilage degradation and joint pain.

The rats were anesthetized by a gaseous mixture of isoflurane and oxygen, and maintained in a supine position. Once the infrapatellar ligament was identified by touch, a single intra-articular injection of monosodium iodoacetate (MIA) was performed in the right knee, after having shaved the skin of the area, while keeping the joint slightly flexed. The amount of MIA injected was equal to 1 mg dissolved in 50 μl of saline solution, having a pH of about 4.5, as measured just before administration. The joint of the left knee was instead injected with 50 μl of saline solution alone, and this represented the internal control.

The treatment involved 4 weekly administrations of sodium chlodronate, followed by one week of follow-up.

The study included 8 treatment groups, each consisting of 10 male Sprague Dawley rats, specifically five treatment groups consisting of OA rats, on which the chlodronate doses of 2, 10, 20, 30, and 40 mg/ml, corresponding to 0.1, 0.5, 1, 1.5, and 2 mg/rat, were tested, and the remaining three groups represented by untreated OA rats, operated but untreated Sham rats, and rats administered only with placebo at pH 4.5.

The injected solutions had the following composition:

| Dose | Weighted amount of sodium chlodronate (lot number: 1209000044) | Dilution |
|---|---|---|
| Placebo | / | 4.5 ml of saline solution + 0.500 ml of 1% sodium |

-continued

| Dose | Weighted amount of sodium chlodronate (lot number: 1209000044) | Dilution |
|---|---|---|
| 2 mg/ml | 10 mg | bicarbonate + 0.058 ml of 1N HCl 3.980 ml of saline solution 0.020 ml of 1% sodium bicarbonate |
| 10 mg/ml | 12.5 mg | 0.974 ml of saline solution 0.026 ml of 1% sodium bicarbonate |
| 20 mg/ml | 25 mg | 0.950 ml of saline solution 0.050 ml of 1% sodium bicarbonate |
| 30 mg/ml | 37.5 mg | 0.922 ml of saline solution 0.078 ml of 1% sodium bicarbonate |
| 40 mg/ml | 50 mg | 0.895 ml of saline solution 0.105 ml of 1% sodium bicarbonate |

The amount of sodium chlodronate to be weighed was corrected by a 1.25 multiplicative factor linked to the hydration of the molecule.

During the treatment period, the animals were regularly checked in relation to the increase in body mass, food intake, and general health conditions. Clinical and hematological analyses were performed at the end of the study. The difference between the size of the edema in the two inflamed knees for all the observation groups, the final serum concentration of CTX-I (C-telopeptide of type I collagen), as a marker of bone turnover, and the final serum concentration of CTX-II (C-telopeptide of type II collagen), as a marker of cartilage turnover were investigated.

Results—Evaluation of the Difference in Edema Size Between the Right and Left Knees.

The measurement of the difference in size of the right and left knee edema (indicated with D and expressed in mm) was performed on anesthetized rats, by using a digital caliper (Digi-max slide caliper W/LCD readout Sigma Aldrich).

The Table 1 below shows the mean values obtained for each observation group.

TABLE 1

| Treatment Group | D, Mean Value (mm) ± SEM |
|---|---|
| OA (not treated) | 0.64 ± 0.091 |
| OA Placebo | 0.65 ± 0.069 |
| Sodium Chlodronate - 2 mg/ml, *p = 0.0117 | 0.37 ± 0.067 |
| Sodium Chlodronate - 10 mg/ml, *p = 0.0004 | 0.28 ± 0.063 |
| Sodium Chlodronate - 20 mg/ml, *p = 0.0002 | 0.27 ± 0.047 |
| Sodium Chlodronate - 30 mg/ml, *p < 0.0001 | 0.11 ± 0.043 |
| Sodium Chlodronate - 40 mg/ml, p = 0.0004 | 0.28 ± 0.033 |
| Sham (not treated), *p = 0.0013 | 0.31 ± 0.041 |

FIG. 1 shows the graph of the values in Table 1.

As it is apparent, a remarkable and statistically significant efficacy of the active ingredient in the reduction of edema could be verified, at all the concentrations tested, in all the observation groups undergoing treatment with sodium chlodronate. A particularly surprising result, in reducing the edema, was observed in particular for the group treated with solutions comprising 30 mg/ml of sodium chlodronate.

These results therefore demonstrate the efficacy of a weekly administration of compositions comprising from 2 to 40 mg/ml of sodium chlodronate in the treatment of OA.

The weekly treatment with sodium chlodronate at a concentration of 30 mg/ml was particularly effective.

Results—Evaluation of CTX-I Final Serum Concentration Value

Considering that CTX-I (C-telopeptide of type I collagen) is a bone turnover marker and its concentration levels are proportional to the osteoclastic activity, the measurement of CTX-I final serum concentration value is a measure of the treatment efficacy. Therefore, the greater the value of CTX-I, the higher the ongoing bone degradation activity, therefore indicating that the therapy was less effective, as it obviously did not allow a reduction in the osteoclastic activity.

Table 2 below shows the results, expressed as CTX-I concentration in pg/ml, in the 7 treatment groups compared to the group of untreated OA rats.

TABLE 2

| | CTX-I Value (pg/ml) | SEM |
|---|---|---|
| OA (not treated) | 5.08 | 0.043 |
| Placebo | 4.98 | 0.045 |
| Sodium Chlodronate - 2 mg/mL | 4.77 | 0.044 |
| Sodium Chlodronate - 10 mg/mL | 4.87 | 0.055 |
| Sodium Chlodronate - 20 mg/mL | 4.6 | 0.103 |
| Sodium Chlodronate - 30 mg/mL, *p < 0.0001 | 4.36 | 0.133 |
| Sodium Chlodronate - 40 mg/mL, *p < 0.0001 | 4.16 | 0.075 |

Figure 2:
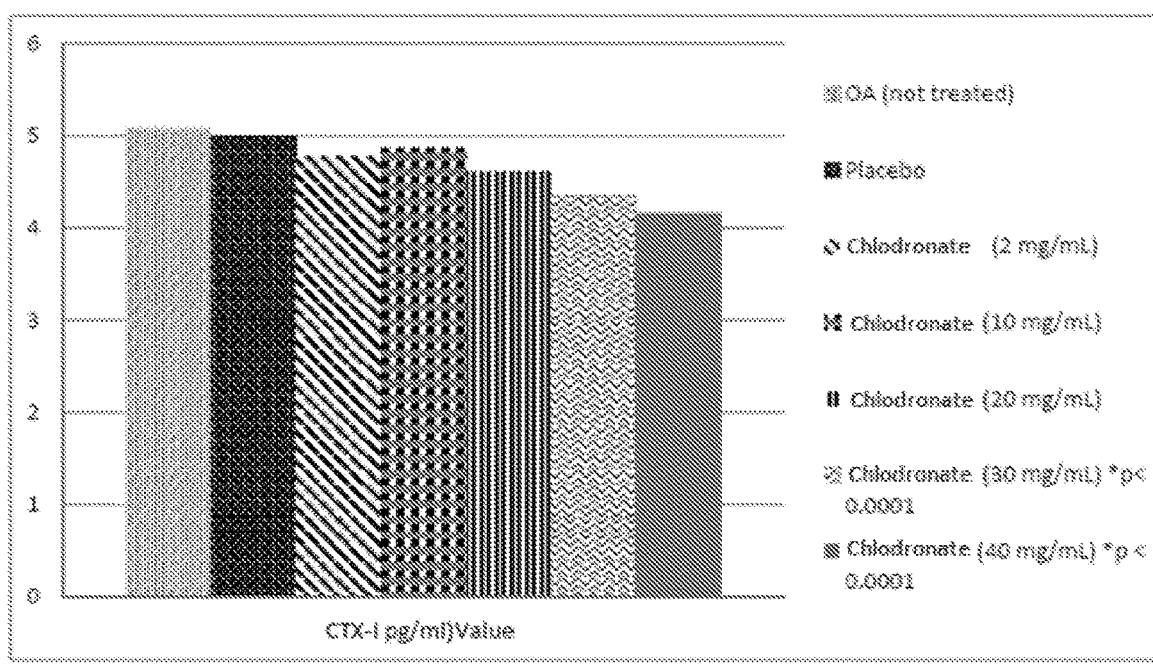
FIG. 2 shows the efficacy results obtained, expressed as the mean value of CTX-I concentration (in pg/ml) in the serum, after weekly treatment with sodium chlodronate at the concentrations of 2, 10, 20, 30 and 40 mg/ml, in the 7 observation groups.

FIG. 2 shows the graph of the values in Table 2.

As it is apparent, a remarkable efficacy of the active ingredient in the reduction of CTX-I serum levels could be verified, at all the concentrations tested, in all the observation groups undergoing treatment with sodium chlodronate. Among other things, it was highly significant also from a statistical point of view.

Another noteworthy observation is the fact that a dose dependent efficacy trend may be assumed, at least above 10 mg/ml, with the best performances obtained in the case of the administration of solutions comprising 30 or 40 mg/ml of sodium chlodronate.

These results therefore demonstrate the efficacy of a weekly administration of compositions comprising from 10 to 40 mg/ml, and preferably in the range from 30 to 40 mg/ml, of sodium chlodronate in the treatment of OA.

Results—Evaluation of CTX-II Final Serum Concentration Value

Considering that CTX-II (C-telopeptide of type II collagen) is a cartilage turnover marker and its concentration levels are proportional to the osteoclastic activity, the measurement of CTX-II final serum concentration value is a measure of the treatment efficacy. Therefore, the greater the value of CTX-II, the higher the ongoing bone degradation activity, therefore indicating that the therapy was less effective, as it obviously did not allow a reduction in the osteoclastic activity.

Table 3 below shows the results, expressed as CTX-II concentration in pg/ml, in the 7 treatment groups compared to the group of untreated OA rats at the end of the study.

TABLE 3

| | CTX-II Value (pg/ml) | SEM |
|---|---|---|
| OA (not treated) | 6.66 | 0.092 |
| Placebo | 7.01 | 0.091 |
| Chlodronate (2 mg/mL) | 6.84 | 0.106 |
| Chlodronate (10 mg/mL) | 6.48 | 0.108 |
| Chlodronate (20 mg/mL) *p = 0.0005 | 5.93 | 0.086 |
| Chlodronate (30 mg/mL) *p < 0.0001 | 5.67 | 0.074 |
| Chlodronate (40 mg/mL) *p = 0.0017 | 5.73 | 0.083 |

Figure 3:
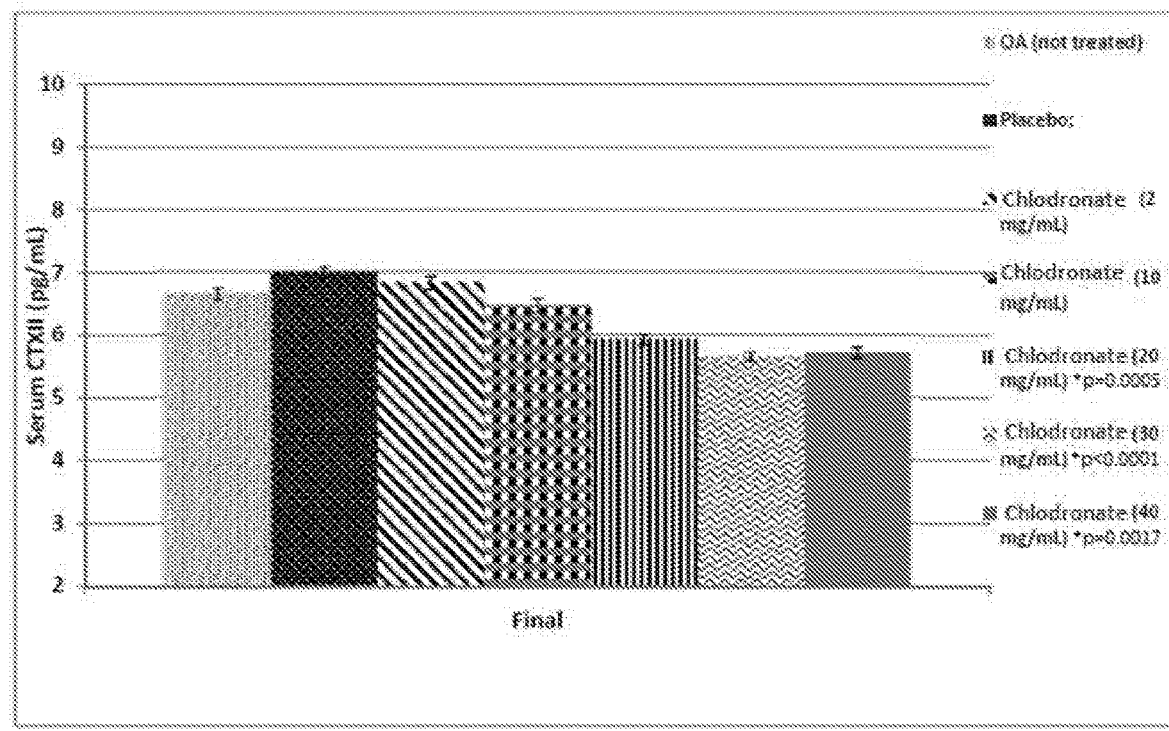
FIG. 3 shows the efficacy results obtained, expressed as the mean value of CTX-II concentration (in pg/ml) in the serum, after weekly treatment with sodium chlodronate at the concentrations of 2, 10, 20, 30, and 40 mg/ml, in the 7 observation groups.

FIG. 3 shows the graph of the values in Table 3.

As it is apparent, a remarkable efficacy of the active ingredient in the reduction of CTX-II serum levels could be verified, at all the concentrations tested, in all the observation groups undergoing treatment with sodium chlodronate. Among other things, the results obtained with all the solutions having a concentration higher than 10 mg/ml resulted to be highly significant also from a statistical point of view.

Another noteworthy observation is the fact that also the results obtained from this test with respect to the observation parameter allow to suppose a dose dependent efficacy trend, already starting from the solution having 2 mg/ml of sodium chlodronate, with the best performances obtained, also in this case, with the administration of solutions comprising 30 or 40 mg/ml of sodium chlodronate.

These results therefore confirm the efficacy of a weekly administration of compositions comprising from 10 to 40 mg/ml, and preferably in the range of 30 to 40 mg/ml, of sodium chlodronate in the treatment of OA.

Results—Evaluation of COMP Final Serum Concentration Value

Considering that the presence of high concentrations of COMP in serum is an indication of the progression of osteoarthritic disease, the measurement of COMP (Cartilage Oligomeric Matrix Protein) final serum concentration is a measure of treatment efficacy.

In fact, COMP seems to play a fundamental role in the formation and structure of articular cartilage, as it has a regulatory function in assembling type II collagen fibers and, together with other matrix proteins, stabilizes the network of collagen fibers. During osteoarthritis, a greater amount of this protein was found in the blood, therefore a higher concentration of COMP in the serum corresponds to a more advanced stage of osteoarthritis degeneration.

Table 4 below shows the results, expressed as COMP concentration in ng/ml, in the 7 treatment groups compared to the group of untreated OA rats.

TABLE 4

|  | COMP Value (ng/ml) | SEM |
|---|---|---|
| OA (not treated) | 6.63 | 0.428 |
| Placebo | 7.29 | 0.64 |
| Chlodronate (2 mg/mL) | 5.46 | 0.589 |
| Chlodronate (10 mg/mL) | 5.52 | 0.549 |
| Chlodronate (20 mg/mL) | 5.24 | 0.538 |
| Chlodronate (30 mg/mL) | 4.9 | 0.579 |
| Chlodronate (40 mg/mL) *p = 0.0027 | 3.52 | 0.496 |

Figure 4:
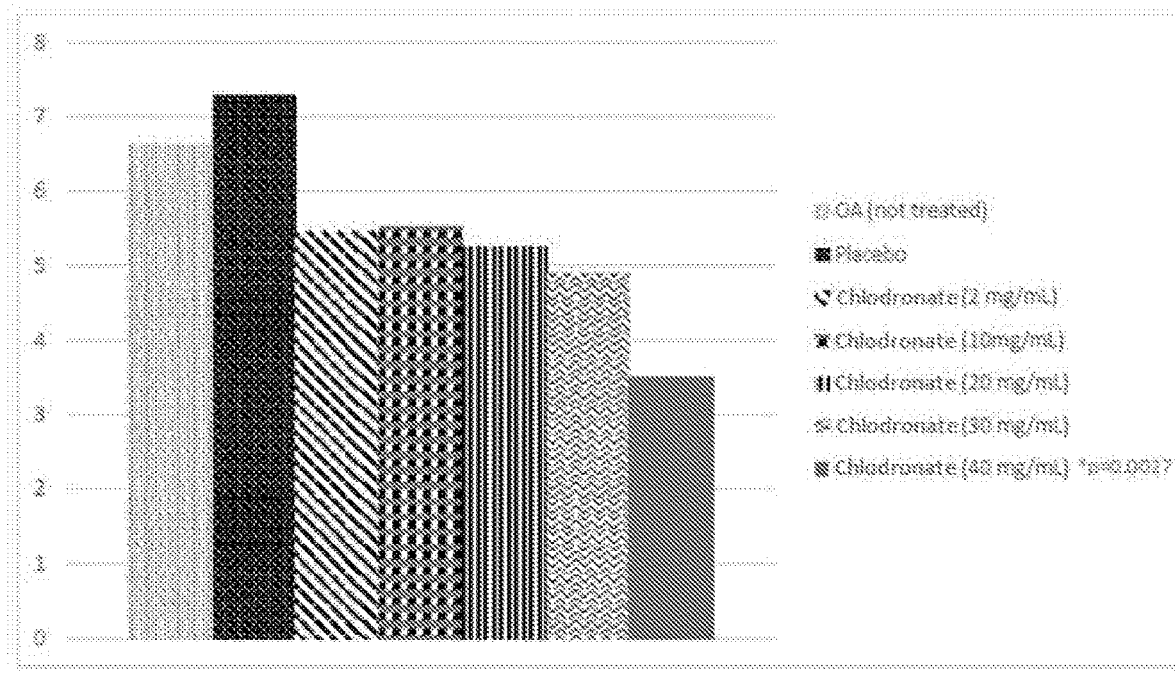
FIG. 4 shows the efficacy results obtained, expressed as the mean value of COMP concentration (in ng/ml) in the serum, after weekly treatment with sodium chlodronate at the concentrations of 2, 10, 20, 30, and 40 mg/ml, in the 7 observation groups.

FIG. 4 shows the graph of the values in Table 4.

As it is apparent, a remarkable efficacy of the active ingredient in the reduction of COMP serum levels could be verified, at all the concentrations tested, in all the observation groups undergoing treatment with sodium chlodronate.

In particular, the experiment reached statistical significance in correspondence to the treatment with solutions comprising sodium chlodronate at a concentration of 40 mg/ml, which proved to be particularly effective in reducing the observation parameter.

Again, the values obtained also in this test show a dose-dependent efficacy trend for solutions comprising concentrations of at least 10 mg/ml of sodium chlodronate, with the best performances obtained also in this case with the administration of solutions comprising 30 or 40 mg/ml of sodium chlodronate, and particularly in the case of the solution comprising 40 mg/ml.

Therefore, also these results confirm the efficacy of a weekly administration of compositions comprising from 10 to 40 mg/ml of sodium chlodronate, and preferably in the range from 30 to 40 mg/ml, in the treatment of OA.

Example 2

In this study, the efficacy of a treatment performed by monthly intra-articular administration of sodium chlodronate on male "Sprague Dawley" rats affected by OA was evaluated. The treatment involved 4 monthly doses of sodium chlodronate, followed by one month of follow-up.

In the experimental model, OA was induced in rats by bilateral anterior cruciate ligament surgical resection in both hind limbs.

A volume of 50 μL of treatment solution, having a pH of about 4.5, as measured just before administration, was injected into the intra-articular cavity of each knee.

The study included 5 treatment groups, each consisting of 10 male rats, specifically two treatment groups consisting of OA rats, on which chlodronate doses of 8 and 12 mg/ml, corresponding to 0.4 and 0.6 mg/rat, were tested, and remaining three groups represented by untreated OA rats, operated but untreated Sham rats, and rats receiving placebo alone.

The injected solutions had the following composition:

Dose of 0 mg/ml of sodium chlodronate (placebo): 5.720 ml of saline solution +0.280 ml of 0.5% sodium bicarbonate+18 μl of 1N HCl;

Dose of 8 mg/ml: 60 mg of sodium chlodronate dissolved in 5.760 ml of saline solution+0.240 mL of 0.5% sodium bicarbonate;

Dose of 12 mg/ml: 90 mg of sodium chlodronate dissolved in 5.640 ml of saline solution+0.360 ml of 0.5% sodium bicarbonate.

During the treatment period, the animals were regularly checked in relation to the increase in body mass, food intake and general health conditions. Clinical and hematological analyses were performed at the end of the study. The quality of cartilage was investigated through histological studies according to the Mankin methodology, by attributing to the observed cartilage values ranging from 0 (normal cartilage) to 15 (seriously damaged cartilage), as well as by evaluating the cartilage area by histomorphometric measurements.

Results—Histopathological Evaluation

Histological examinations were carried out on 5-7 μm slices of frontal sections of the right knee, soaked in paraffin, according to the modified Mankin Scoring System (Gerwin et Al, Osteoarthritis and Cartilage 18 (2010) S24-S34; Kraus V B, et al Osteoarthritis and Cartilage 18 (Suppl 3) (2010) S24-S34), stained with Haematoxylin-Eosin (H&E), Masson Goldner Trichrome (for cellular architecture) and with Safranin-O-Fast Green (for cartilage structure).

According to this evaluation scale, whose values are always comprised between 0 (normal cartilage) and 15 (seriously damaged cartilage), lower values of this index correspond to a state of greater cartilage health.

Table 5 below shows, for each observation group, the mean values of the Mankin index, evaluated as per procedure, by assigning a score to each of the five observation parameters (i.e. articular cartilage structure, proteoglycan content, cellularity, integrity of tidemark, and additional features, related to the presence or absence of osteophytes and their size):

TABLE 5

| Treatment | Mankin Index Mean Value ± SEM |
|---|---|
| OA (not treated) | 5.1 ± 0.623 |
| OA Placebo | 5.2 ± 0.327 |
| Sodium Chlodronate 8 mg/ml | 4.9 ± 0.458 |
| Sodium Chlodronate 12 mg/ml | 2.6 ± 0.618 |
| Sham (not treated) | 1.2 ± 0.389 |

Figure 5:
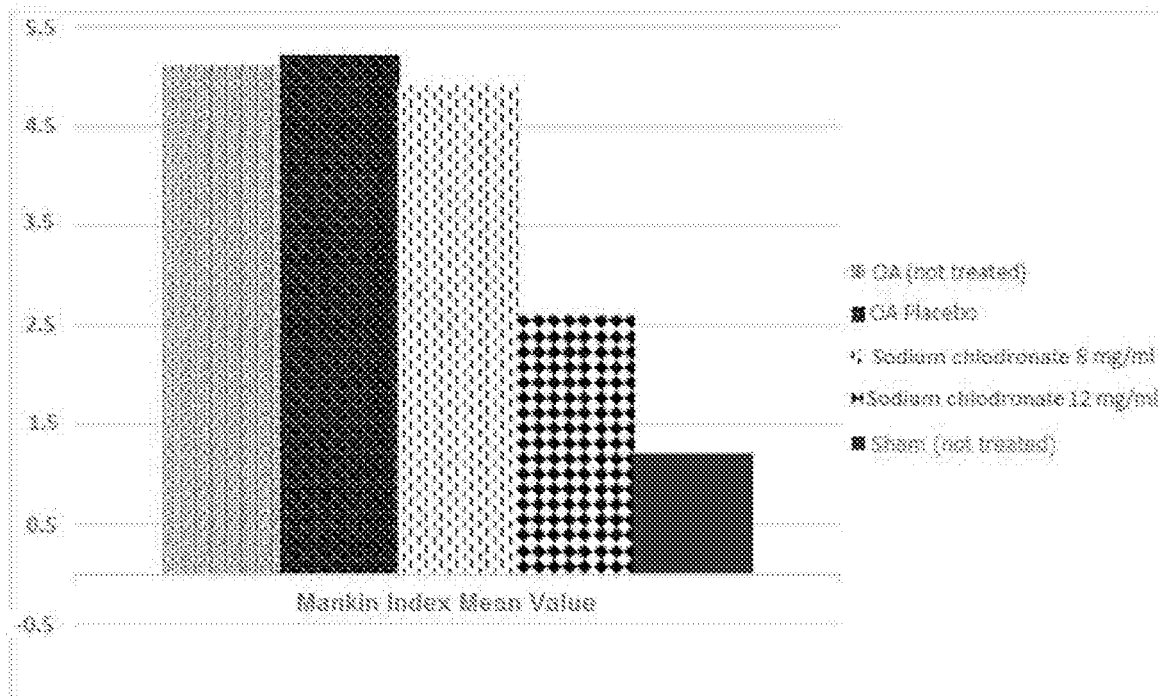
FIG. 5 shows the efficacy results obtained, expressed as Mankin Index, in the experiment performed on OA rats following monthly treatment with sodium chlodronate at the concentration of 8 and 12 mg/ml.

FIG. 5 shows the graph of the values in Table 5.

As it is apparent, both groups undergoing treatment with sodium chlodronate exhibited a lower value of the Mankin index, thus demonstrating the positive effect on cartilage due to chlodronate action. This effect resulted to be particularly marked at 12 mg/ml dosage.

These results therefore confirm the efficacy of a monthly administration of chlodronate compositions, in dosages equal to at least 8 mg/ml. The efficacy has also proved to be increasing with increasing sodium chlodronate concentration used.

Results—Histomorphometric Evaluation of the Cartilage Area

Histomorphometric quantitative measurements of the cartilage area were performed using Image-Pro Plus 4.1 software for windows (Media Cybernetics, Maryland, USA). The images were examined by Zeiss Axioskop microscope (2.5×, light=5) and a JVC Color camera (TK-1280 E).

The results obtained for each observation group are shown in Table 6 below:

TABLE 6

| Treatment | Cartilage Area Average Value ± SEM |
|---|---|
| OA (not treated) | 415 ± 171.0 |
| OA Placebo | 422 ± 136.3 |
| Sodium Chlodronate 8 mg/ml | 486 ± 157.7 |
| Sodium Chlodronate 12 mg/ml | 435 ± 125.9 |
| Sham (not treated) | 426 ± 55.2 |

Figure 6:
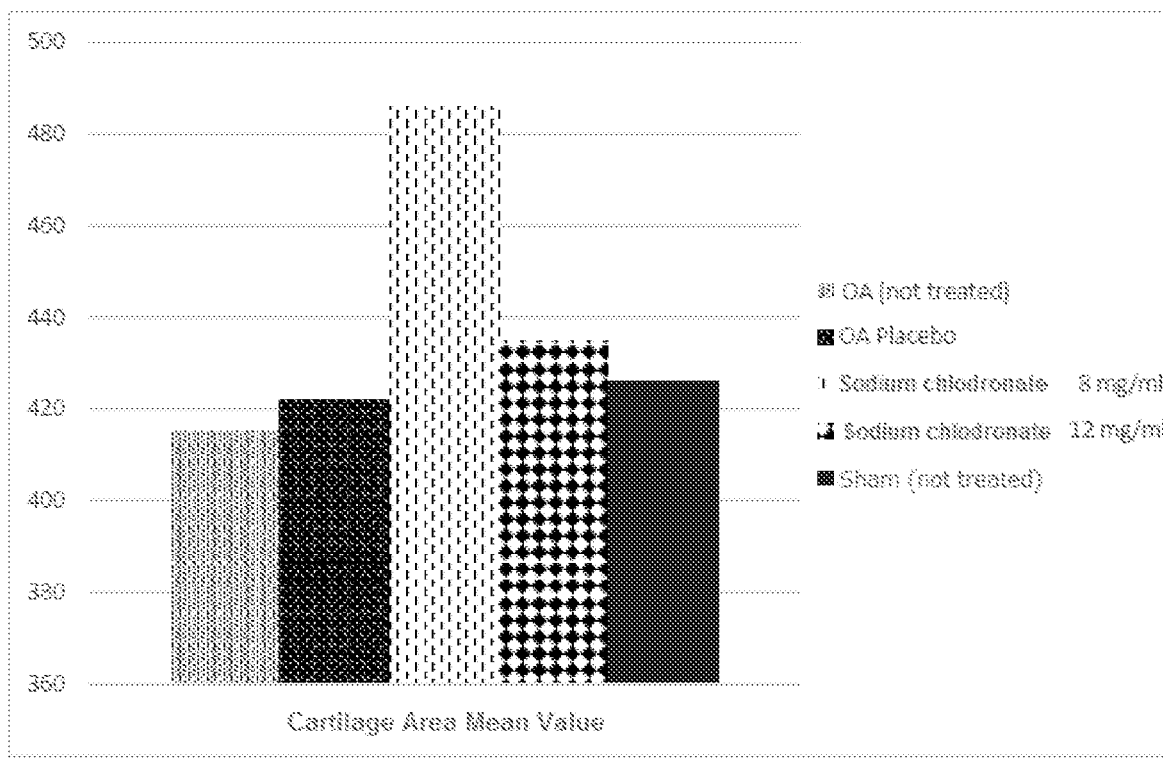
FIG. 6 shows the efficacy results obtained, expressed as the cartilage area value, in the experimentation performed on OA rats following monthly treatment with sodium chlodronate at the concentration of 8 and 12 mg/ml.

FIG. 6 shows the graph of the values in Table 6.

As it is apparent, both groups undergoing treatment with sodium chlodronate exhibited a higher value of the cartilage area, thus demonstrating the positive effect on cartilage due to the action of chlodronate. This effect resulted to be particularly marked at 8 mg/ml dosage.

These results also confirm the efficacy of a monthly administration of chlodronate compositions, at dosages equal to at least 8 mg/ml.

Example 3

In this study the pharmacokinetics of $^{14}$C-Chlodronate was evaluated, and the localization of the labeled compound in the knee joint following a single intra-articular injection of 0.1 mg of $^{14}$C-Chlodronate, administered as aqueous solution in a concentration of 2 mg/ml, in sham and osteoarthritic rat models was verified.

The pharmacokinetic parameters of $^{14}$C-Chlodronate were determined by measuring the radioactivity of blood samples collected at different timepoints from the time of injection.

The localization of the labeled compound in the knee joint was determined by leg x-rays. The fitting of radioactivity concentrations, expressed in µCi/g, was performed by using standard curves.

This study showed that in the osteoarthritis rat model, after only 30 minutes from the injection, the radioactivity was already mainly localized only in the articular cartilage, with a concentration of about 40 µCi/g compared to concentrations, even lower than 1 µCi/g, found both in the synovial cavity and in the femoral and tibial bone. Furthermore, after a few hours from the injection, the concentration of $^{14}$C-Chlodronate in the blood was already very modest, practically negligible.

The radioactivity, concentrated therefore almost exclusively in the cartilage, also showed a very slow decrease over time; starting from 72 hours the values tended to stabilize, and 168 hours after the injection (i.e. 7 days after the injection), it was possible to find a radioactivity mean value still equal to about 25 µCi/g, i.e. still equal to more than 62% of the value found half an hour after the injection.

Table 7 below shows the radioactivity values measured in the femoral and tibial cartilage of osteoarthritic rats, expressed as µCi/g, at different timepoints from the time of intra-articular injection of $^{14}$C-Chlodronate.

| | t = 30 minutes | t = 6 hours | t = 24 hours | t = 72 hours | t = 168 hours |
|---|---|---|---|---|---|
| Femoral Articular Cartilage | 42.649 ± 3.763 | 36.163 ± 4.315 | 34.712 ± 1.861 | 25.561 ± 0.984 | 28.020 ± 0.491 |
| Tibial Articular Cartilage | 36.935 ± 2.517 | 27.299 ± 3.897 | 27.840 ± 1.259 | 22.331 ± 3.953 | 21.165 ± 1.708 |

The results of this kinetic study thus confirmed the high affinity of chlodronate for the cartilage, which resulted in rather long residence times on site even one week after the injection, with persisting high concentrations of chlodronate in both femoral and tibial articular cartilage, thus confirming the rationale for a drug administration frequency of at least once a week.

In addition, at about two weeks after the injection, the data in Table 7, that can be mathematically approximated by a first order exponential curve, would point out a concentration of $^{14}$C-Chlodronate in both femoral and tibial cartilage, expressed as µCi/g, always about 40% higher of the value measured at t=30 minutes, and specifically, with relation to the femoral articular cartilage, said residual $^{14}$C-Chlodronate concentration, expressed as µCi/g, would be equal to about 18.92, i.e. equal to about 44.36% of the value measured at t=30 minutes.

Surprisingly, at about 1 month after injection, the residual value of $^{14}$C-Chlodronate concentration in the cartilage would still be significantly high for both observation sites. In the specific case of the femoral articular cartilage, said residual value of $^{14}$C-Chlodronate concentration, expressed as µCi/g, would even still be equal to about 8.78 µCi/g, i.e. still equal to about 24.27% of the value measured at t=30 minutes, therefore still a very significant residual value.

These data therefore provide further evidence of the possibility of using the drug even with a biweekly or monthly frequency.

It is apparent that the use of compositions in the form of unitary dosage form of sodium chlodronate, chlodronic acid or other salts thereof, and suitable excipients, administered intra-articularly, biweekly or monthly, and preferably monthly, are to be considered particularly advantageous, because of their greater acceptance by the patient, given the intrinsic pain of such injections.

Example 4

With the aim to determine also the maximum dosages of chlodronate administrable in a single intra-articular injection, the local tolerability of intra-articular injections of sodium chlodronate, after repeated administration in the right knee of male and female Sprague Dawley rats, was investigated in this study.

Groups consisting of 5 male rats and 5 female rats each were subjected to intra-articular administration of aqueous solutions comprising 4, 14 and 40 mg/ml of sodium chlodronate (corresponding to dosages of 0.2, 0.7, and 2 mg/rat).

Each animal received a total of 12 intra-articular injections of chlodronate or placebo, administered as 3 injections per week (on Monday, Wednesday, and Friday) for 4 consecutive weeks. For the high dose group and the control group, the relative control groups with the same numerosity as the main groups were also provided.

During the treatment period, the animals were regularly checked in relation to the increase in body mass, food intake, and general health conditions.

At the end of the study, neither mortality nor behavioral or clinical changes related to the treatment with sodium chlodronate were recorded. Body weight and food consumption were normal for all animals.

At the end of the study, hematological analyses, chemical-clinical analyses, urino-analysis, and necropsy were performed.

No abnormalities were detected on necropsy examination, and hematological analyzes with the differential count of the leucocytes and urinary analyses showed no alterations due to the treatment.

In males subjected to the highest dose, sodium chlodronate produced only a condition of initial hepatic suffering characterized by a significant increase in ALP and ALT values in serum, and in females of the same group a slight renal suffering with an increase in electrolyte serum concentration.

Based on the results of this study, it was therefore possible to reasonably conclude that the repeated intra-articular administration was well tolerated by rats, and that the 40 mg/ml dose was the Maximum Tolerated Dose (MTD), the intermediate dose of 14 mg/ml could be considered instead the NOAEL dose (No Observed Adverse Effect Level).

The study thus confirmed the possibility of administering compositions comprising up to 40 mg/ml of sodium chlodronate in a single dose.

Thanks to the studies carried out and described above, the inventors have therefore surprisingly found that high unitary dosage forms of sodium chlodronate, preferably between 5 and 40 mg, resulted to be particularly effective in curing or treating OA, when administered intra-articularly weekly, biweekly or monthly.

For the purposes of the present invention, said compositions are preferably administered monthly.

Example 5

Certain compositions of the invention were prepared in unitary dosage form, in the form of an aqueous solution, for weekly, biweekly or monthly administration, comprising sodium chlodronate in tetrahydrate form, whose quali-quantitative compositions and pH, osmolality, and density values, are shown in Table 8 below.

TABLE 8

| Component | Amount per unitary dosage form (mg) | | | | |
|---|---|---|---|---|---|
| Sodium Chlodronate | 5.00 | 10.00 | 20.00 | 30.00 | 40.00 |
| (in tetrahydrate form) | 6.25 | 12.50 | 25.00 | 37.50 | 50.00 |
| Excipients | | | | | |
| Sodium Chloride | 9.4 | 10.03 | 7.428 | 4.732 | 2.598 |
| Sodium Hydrogen Carbonate | 0.125 | 0.25 | 0.4 | 0.6 | 1 |
| Water for injection | up to 1 ml | up to 1 ml | up to 1 ml | up to 1 ml | up to 1 ml |
| Parameters | | | | | |
| pH | 4.6 | 4.5 | 4.4 | 4.4 | 4.5 |
| Osmolality (mOsm/Kg) | 395 | 400 | 388 | 408 | 413 |
| Density (g/ml) | 1.014 | 1.016 | 1.021 | 1.027 | 1.032 |

As it is apparent from the table, all the compositions prepared had particularly high osmolality values. Osmolalities were determined by GONOTEC Osmometer, OSMOMAT 3000-D model, serial number 3000150264 according to USP, chapter 785 under the title "Osmolality and Osmolarity".

Said formulations were subjected to a stability study according to the ICH guidelines, under the following three specific conditions: 25° C.±2° C./60% RH±5% RH (long-term conditions), 30° C.±2° C./65% RH±5% RH (intermediate conditions), and 40° C.±2° C./75% RH±5% RH (accelerated conditions).

After 3 months conditioning, the following parameters were assessed: appearance, color, and clarity of the solution, pH, amount of particulate matter, concentration of sodium chlodronate, and concentration of any phosphates and other degradation products.

All measured parameters were found to comply with the specifications, even under accelerated test conditions.

The stability study has therefore surprisingly confirmed the possibility of formulating stable aqueous solutions with a high concentration of sodium chlodronate, specifically in concentrations comprised between 5 and 40 mg/ml, when said aqueous solutions have osmolality values comprised between 380 and 420 mOsm/Kg.

The compositions of the invention, in unitary dosage form, comprising sodium chlodronate in the range from 5 to 40 mg/ml, and characterized by an osmolality in the range from 380 to 420 mOsm/kg, preferably in the range from 385 to 415 mOsm/kg, have thus proved to be stable and, therefore, particularly advantageous for the purposes of the invention.

The inventors have therefore demonstrated with the present invention that a new type of therapeutic approach for curing and treating OA, and in particular pain symptoms of OA, is available today, thanks to the verified possibility and efficacy of the administration by intra-articular route of unitary dosage forms ranging from 5 to 40 mg of sodium chlodronate, or an equivalent amount of chlodronic acid or other salts thereof, and appropriate excipients to be administered weekly, biweekly or monthly, and preferably monthly.

The inventors have also demonstrated that said compositions having a high concentration of sodium chlodronate are particularly stable in aqueous solution, if formulated so as to obtain osmolality values comprised between 380 and 420 mOsm/Kg, preferably between 385 and 415 mOsm/Kg.

According to the present invention, it is therefore possible to produce vials, bottles, carpules and single-dose syringes pre-filled with said compositions, also in the form of an aqueous solution.

Advantageously said vials, bottles, carpules and pre-filled single-dose syringes, containing unitary dosage forms of the drug, may be administered monthly, biweekly or weekly by intra-articular route, to patients affected by OA, in particular for the treatment of pain symptoms.

Preferably, said vials, bottles, carpules or pre-filled syringes may be marketed in the form of a kit comprising them in the number of 1, 2 or 4.

The invention claimed is:

1. A method for the treatment of osteoarthritis (OA), wherein said method comprises the step of administering a composition comprising from 5 to 40 mg of sodium clodronate, or an equivalent amount of clodronic acid, or other pharmaceutically acceptable salts thereof, and wherein said composition is in a unitary dosage form administered intra-articularly once monthly, once biweekly or once weekly, wherein said sodium clodronate is in tetra-hydrated form.

2. The method according to claim 1, wherein said treatment is the treatment of pain symptoms of osteoarthritis (OA).

3. The method according to claim 1, wherein said composition comprises from 5 to 20 mg of sodium clodronate, or an equivalent amount of clodronic acid, or other pharmaceutically acceptable salts thereof.

4. The method according to claim 3, wherein said composition comprises from 8 to 20 mg of sodium clodronate, or an equivalent amount of clodronic acid, or other pharmaceutically acceptable salts thereof.

5. The method according to claim 1, wherein said composition comprises from 30 to 40 mg of sodium clodronate, or an equivalent amount of clodronic acid, or other pharmaceutically acceptable salts thereof.

6. The method according to claim 1, wherein said composition is administered intra-articularly in a unitary dosage form once monthly.

7. The method according to claim 1, wherein said composition is administered intra-articularly in a unitary dosage form once biweekly.

8. The method according to claim 1, wherein said composition is administered intra-articularly in a unitary dosage form once weekly.

9. The method according to claim 1, wherein said composition in a unitary dosage form is in an aqueous solution form.

10. The method according to claim 9, wherein said composition in an aqueous solution form has a volume from 1 to 3 ml.

11. The method according to claim 9, wherein said composition in an aqueous solution form has a pH value from 3.5 to 5.5.

12. A single dose medicament consisting of a container selected from the group consisting of a vial, a bottle, a carpule, and a pre-filled syringe, and a composition contained in said container and comprising from 5 to 40 mg of sodium clodronate, or an equivalent amount of clodronic acid, or other pharmaceutically acceptable salts thereof, and, optionally, pharmaceutically acceptable excipients, wherein said sodium clodronate is in tetra-hydrated form.

13. The single dose medicament according to claim 12, wherein the composition of the single dose medicament is in the form of a ready-to-use aqueous solution.

14. The single dose medicament according to claim 13, wherein the aqueous solution has a volume from 1 to 3 ml.

15. The single dose medicament according to claim 12, wherein the composition of the single dose medicament is in the form of a ready-to-use aqueous solution comprising from 30 to 40 mg of sodium clodronate in a volume of 1 ml.

16. A method for the treatment of osteoarthritis comprising the step of administering a single dose medicament according to claim 12, wherein said single dose-medicament is administered intra-articularly once monthly.

17. A kit comprising from 1 to 4 single dose-medicaments according to claim 12.

18. The method according to claim 10, wherein said aqueous solution form has a volume equal to 1 ml.

19. The method according to claim 11, wherein said aqueous solution form has a pH value from 4.0 to 5.0.

20. The method according to claim 11, wherein said aqueous solution form has a pH value from 4.3 to 4.7.

21. The single dose-medicament according to claim 14, wherein the aqueous solution has a volume equal to 1 ml.

22. The kit according to claim 17 comprising from 1 to 2 single dose-medicaments.

23. The kit according to claim 17, comprising 1 dose-medicament.

* * * * *